United States Patent
Kim et al.

(10) Patent No.: US 12,178,837 B2
(45) Date of Patent: Dec. 31, 2024

(54) COMPOSITION FOR SKIN-WHITENING OR PREVENTING OR IMPROVING SKIN WRINKLES COMPRISING GREEN TEA EXTRACT WHICH HAS MODIFIED AMOUNTS OF INGREDIENTS

(71) Applicant: AMOREPACIFIC CORPORATION, Seoul (KR)

(72) Inventors: Juewon Kim, Yongin-si (KR); Si Young Cho, Yongin-si (KR); Hyungsu Kim, Yongin-si (KR); Wonseok Park, Yongin-si (KR); Joonho Choi, Yongin-si (KR); Dong Hyun Kim, Yongin-si (KR); Jaewon You, Yongin-si (KR); Miyoung Park, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 18/520,281

(22) Filed: Nov. 27, 2023

(65) Prior Publication Data

US 2024/0091296 A1    Mar. 21, 2024

Related U.S. Application Data

(62) Division of application No. 16/742,812, filed on Jan. 14, 2020, now Pat. No. 11,896,640.

(30) Foreign Application Priority Data

Jan. 15, 2019   (KR) .................. 10-2019-0005248
Jan. 15, 2019   (KR) .................. 10-2019-0005271

(51) Int. Cl.
| | | |
|---|---|---|
| A61K 36/82 | (2006.01) | |
| A23L 33/105 | (2016.01) | |
| A61K 8/97 | (2017.01) | |
| A61Q 19/02 | (2006.01) | |
| A61Q 19/08 | (2006.01) | |

(52) U.S. Cl.
CPC ............ *A61K 36/82* (2013.01); *A23L 33/105* (2016.08); *A61K 8/97* (2013.01); *A61Q 19/02* (2013.01); *A61Q 19/08* (2013.01); *A61K 2800/782* (2013.01)

(58) Field of Classification Search
None
See application file for complete search history.

(56) References Cited

U.S. PATENT DOCUMENTS

| | | |
|---|---|---|
| 11,110,145 B2 | 9/2021 | Kim et al. |
| 2012/0156150 A1 | 6/2012 | Kim et al. |
| 2014/0377201 A1 | 12/2014 | Lee et al. |
| 2016/0175217 A1 | 6/2016 | Kim et al. |
| 2019/0091275 A1 | 3/2019 | Kim et al. |
| 2019/0091276 A1 | 3/2019 | Kim et al. |

FOREIGN PATENT DOCUMENTS

| | | |
|---|---|---|
| CN | 106456521 A1 | 2/2017 |
| JP | 2006-94825 A | 4/2006 |
| JP | 2007-112717 A | 5/2007 |
| KR | 10-2007-0028903 A | 3/2007 |
| KR | 10-2008-0006895 A | 1/2008 |
| KR | 10-2008-0101419 A | 11/2008 |
| KR | 10-2017-0000490 A | 1/2017 |
| KR | 10-2017-0107943 A | 9/2017 |
| KR | 10-1863053 B1 | 5/2018 |
| WO | 01/49285 A1 | 7/2001 |
| WO | 2019/088412 A1 | 5/2019 |

OTHER PUBLICATIONS

Tomoko Shimamura et al., "Relationship between catechin content and antioxidant capacity in natural food additive tea extract," Japanese Journal of Food Chemistry and Safety 24(1): 10-15 (2017).
Office Action for Japanese Patent Application No. 2019-226797 (Sep. 29, 2023).
Gary J. Fisher et al., "Molecular basis of sun-induced premature skin ageing and retinoid antagonism", Letters to Nature, vol. 379, pp. 335-339 (Jan. 25, 1996).
Masamitsu Ichihashi, Fragrance Journal, vol. 32, pp. 24 (2004).
Extended European Search Report from European Application No. 19213633.1, mailed Jun. 12, 2020.
"Tea in health and disease prevention", edited by Vitor Preddy, Academic Press: 215 (2012).
Wang H et al., "Epimerisation of catechins in green tea infusions", Food Chemistry 70: 337-344 (2000).
Moita O et al., "Safety assessment of heat-sterilized green tea catechin preparation: a 6-month repeat-dose study in rats", Food and Chemical Toxicology 47: 1760-1770 (2009).
Seto R et al., "Preparation of Epimers Tea Catechins by Heat Treatment", Bioscience, Biotechnology, and Biochemistry 61:1434-1439 (1997).
Vuong Q.V. et al., "Optimizing conditions for the extraction of catechins from green tea using hot water", Research Article, J. Sep. Sci. 34: 3099-3106 (2011).
Demir E. et al., "Comparison of Some Extraction Methods for Isolation of Catechins and Caffeine from Turkish Green Tea", International Journal of Secondary Metabolite vol. 2, Issue 2: 16-25 (2015).

(Continued)

*Primary Examiner* — Michael V Meller
(74) *Attorney, Agent, or Firm* — Merchant & Gould P.C.

(57) ABSTRACT

Disclosed is to provide a composition for skin-whitening or preventing or improving skin wrinkles, comprising a green tea extract which has modified amounts of ingredients. More specifically, the extract and composition according to one aspect of the present disclosure are derived from natural plants that cause less irritation to the skin and are eco-friendly, thus they are safe, and thereby the extract and composition can exhibit excellent effects of effectively inhibiting melanin production and tyrosinase activity and preventing or improving skin whitening, and can exhibit excellent effects of effectively inhibiting the expression of MMP-1 and preventing or improving skin wrinkles.

9 Claims, 3 Drawing Sheets

(56) References Cited

OTHER PUBLICATIONS

Office Action for Chinese Patent Application No. 202010035802.1 (Dec. 13, 2022).
Phung et al., Effect of green tea catechins with or without caffeine on anthoropometric measures: a systematic review and meta-analysis 1-3, Am J. Clin. Nutr 91: 73-81 (2010).
Office Action issued in the corresponding Korean Patent Application No. 10-2019-0005271, May 30, 2024.
Sang Nam Kim et al., "Comparison in Collagen Synthetic Abilities of Water Extracts of Green Tea, White Tea and Black Tea in Human Dermal Fibroblasts", Journal of Investigative Cosmetology, 2012, vol. 8, No. 4, pp. 227-233.
Jeong Kee Kim et al., "Effect of Heat-epimerized-catechin-mixture Rich in Gallocatechin-3-gallate on Skin Barrier Recovery", J. Soc. Cosmet. Scientists Korea, 2008, vol. 34, No. 2, pp. 93-99.

COMPOSITION FOR SKIN-WHITENING OR PREVENTING OR IMPROVING SKIN WRINKLES COMPRISING GREEN TEA EXTRACT WHICH HAS MODIFIED AMOUNTS OF INGREDIENTS

CROSS-REFERENCE TO RELATED APPLICATION

This application is a Divisional of U.S. patent application Ser. No. 16/742,812, filed on Jan. 14, 2020, which claims the priority of Korean Patent Application No. 10-2019-0005248, filed on Jan. 15, 2019 and Korean Patent Application No. 10-2019-0005271, filed on Jan. 15, 2019 and all the benefits accruing therefrom under 35 U.S.C. § 119, the contents of which in its entirety are herein incorporated by reference.

BACKGROUND

1. Field

The present disclosure relates to a composition for skin-whitening or preventing or improving skin wrinkles, comprising a green tea extract which has modified amounts of ingredients.

2. Description of the Related Art

The causes of the skin aging phenomenon can be greatly classified into two: internal factors such as gene variation, structure change, etc. of cells, and external factors such as ultraviolet rays, humidity, etc. (Masamitsu Ichihashi, Fragrance Journal, Vol. 32, No. 5, 24 to 30). In the skin damaged by these internal and external factors, the phenomenon such as reduction of skin regeneration, change of the environment surrounding the cells, and weakening of the intercellular networks occurs, which results in scattering of the skin structure, and thereby, the phenomenon such as skin elasticity loss, keratinization, wrinkle generation, skin transparency degradation and skin atrophia, etc. occurs.

The biggest change in aged skin is caused by a reduction of the growth factor that was active in younger skin. Since growth factors act as the first switch in the regeneration process in the skin, the reduction of growth factors in the skin causes deterioration of various functions in the skin, resulting in the loss of the components in the skin and the breakdown of the skin structure.

In addition, the phenomenon of aging due to ultraviolet rays is called photoaging, and it has been known that this photoaging phenomenon generates reactive oxygen radicals (ROS) inside the cell by ultraviolet rays, and the active oxygen promotes the synthesis of proteolytic enzymes (MMP-1, MMP-3 and MMP-9, etc.) that degrade proteins such as collagen and elastin, which are elastic fibers of a dermal layer, through a signaling system causing an inflammatory reaction (Fisher G J et al., Nature, Vol. 379, 335-339), thereby reducing elasticity of the dermal layer which causes skin wrinkles. Therefore, in order to prevent such skin aging phenomenon and maintain a healthier and more elastic skin, research activities have been steadily conducted to develop a bioactive substance having an anti-wrinkle effect. For example, in 1995, tretinoin (trans-retinoic acid) was approved by the US FDA as a medicine for the improvement of photo-aged skin, and as Retinol, which has low side effects, began to be used in cosmetic raw materials in the late 1990s, wrinkle improvement cosmetics have been started to be released. Since then, female hormone-like substances and antioxidants derived from various plants have been introduced into cosmetics as raw materials for improving wrinkles. As such, consumers' interest in and demand for cosmetics related to skin aging are increasing rapidly, but side effects of synthetic functional cosmetics have continuously occurred, and therefore, research on the development of cosmetics using natural products that are effective and nontoxic has been actively conducted.

On the other hand, when exposed to ultraviolet rays, the skin has physical and chemical defense factors, and has a mechanism of action to minimize skin disorders caused by various photochemical reactions. The stratum corneum of the skin reduces energy by reflecting and diffusing ultraviolet rays, and melanin, superoxide dismutase (SOD), and other antioxidants protect against skin disorders by absorbing the ultraviolet rays that are penetrated into the skin and reducing its energy or by eliminating active oxygen that the ultraviolet rays secondarily generate. However, various skin disorders occur when a living body receives a large amount of ultraviolet rays exceeding the above-described defensive factors or its ability decreases as the body ages.

The distribution and amount of melanin in the skin occupy the largest proportion of skin color determinants. Melanin plays an important role in forming a cap-like structure around the nucleus to protect genes from ultraviolet rays and in protecting proteins in cells by eliminating free radicals. Enzymes that degrade such melanin do not exist in body, and melanin are removed together from the skin as keratinocytes is aged and fully functioned and fall off the epidermis. However, when melanin is produced more than necessary, it causes hyperpigmentation such as blemishes, freckles, and spots, which may cause cosmetically bad results.

Several factors have been known as affecting melanin production, and the increase of melanin production caused by ultraviolet rays and the resulting pigmentation are very important in cosmetic field. The basic mechanisms of drugs mixed in whitening cosmetics for the purpose of preventing pigmentation include: inhibiting tyrosinase action, inhibiting tyrosinase production, inhibiting melanin-producing intermediates, inhibiting melanin reduction and inhibiting photooxidation, promoting melanin excretion, and cutting ultraviolet rays, and the like.

There is an increasing need for prevention and improvement of skin pigment abnormalities and hyperpigmentation, and it has been necessary to develop a whitening product that suppresses excessive melanin production. Specific examples thereof include inhibitors such as kojic acid, arbutin that inhibit tyrosinase activity, hydroquinone, vitamin A, vitamin C, and derivatives thereof, etc. However, their use has been limited due to problems such as insufficient whitening effect, stability in the formulation and safety to the skin. Therefore, researches on raw materials derived from natural products that are highly effective for skin whitening, easy to formulate, and safe for skin are being actively conducted.

SUMMARY

The object of the present disclosure is to provide a composition derived from natural plants, which is nontoxic and is effective for preventing or improving skin wrinkles, and a method for preparing the same.

In addition, the object of the present disclosure is to provide a composition derived from natural plants, which is nontoxic and is effective for skin-whitening, and a method for preparing the same.

In order to achieve the aforementioned objects, in one aspect, the present disclosure provides a composition for preventing or improving skin wrinkles, comprising, as an effective ingredient, a green tea extract containing 4 to 15 wt. % of (−)-gallocatechin gallate (GCG) and 4 to 15 wt. % of (−)-epigallocatechin gallate (EGCG), on the basis of the total weight of the extract.

In another aspect, the present disclosure provides a composition for skin-whitening, comprising, as an effective ingredient, a green tea extract containing 4 to 15 wt. % of (−)-gallocatechin gallate (GCG) and 4 to 15 wt. % of (−)-epigallocatechin gallate (EGCG), on the basis of the total weight of the extract.

In one another aspect, the present disclosure provides a use of a green tea extract containing 4 to 15 wt. % of (−)-gallocatechin gallate (GCG) and 4 to 15 wt. % of (−)-epigallocatechin gallate (EGCG), on the basis of the total weight of the extract, for the preparation of the composition for preventing or improving skin wrinkles.

In one another aspect, the present disclosure provides a use of a green tea extract containing 4 to 15 wt. % of (−)-gallocatechin gallate (GCG) and 4 to 15 wt. % of (−)-epigallocatechin gallate (EGCG), on the basis of the total weight of the extract, for the preparation of the composition for skin-whitening.

In one another aspect, the present disclosure provides a green tea extract containing 4 to 15 wt. % of (−)-gallocatechin gallate (GCG) and 4 to 15 wt. % of (−)-epigallocatechin gallate (EGCG), on the basis of the total weight of the extract, for use in preventing or improving skin wrinkles.

In one another aspect, the present disclosure provides a green tea extract containing 4 to 15 wt. % of (−)-gallocatechin gallate (GCG) and 4 to 15 wt. % of (−)-epigallocatechin gallate (EGCG), on the basis of the total weight of the extract, for use in skin-whitening.

In one another aspect, the present disclosure provides a method for preventing or improving skin wrinkles, comprising administering, to a subject in need thereof, a green tea extract containing 4 to 15 wt. % of (−)-gallocatechin gallate (GCG) and 4 to 15 wt. % of (−)-epigallocatechin gallate (EGCG), on the basis of the total weight of the extract.

In one another aspect, the present disclosure provides a method for skin-whitening, comprising administering, to a subject in need thereof, a green tea extract containing 4 to 15 wt. % of (−)-gallocatechin gallate (GCG) and 4 to 15 wt. % of (−)-epigallocatechin gallate (EGCG), on the basis of the total weight of the extract.

DETAILED DESCRIPTION

Figure 1:
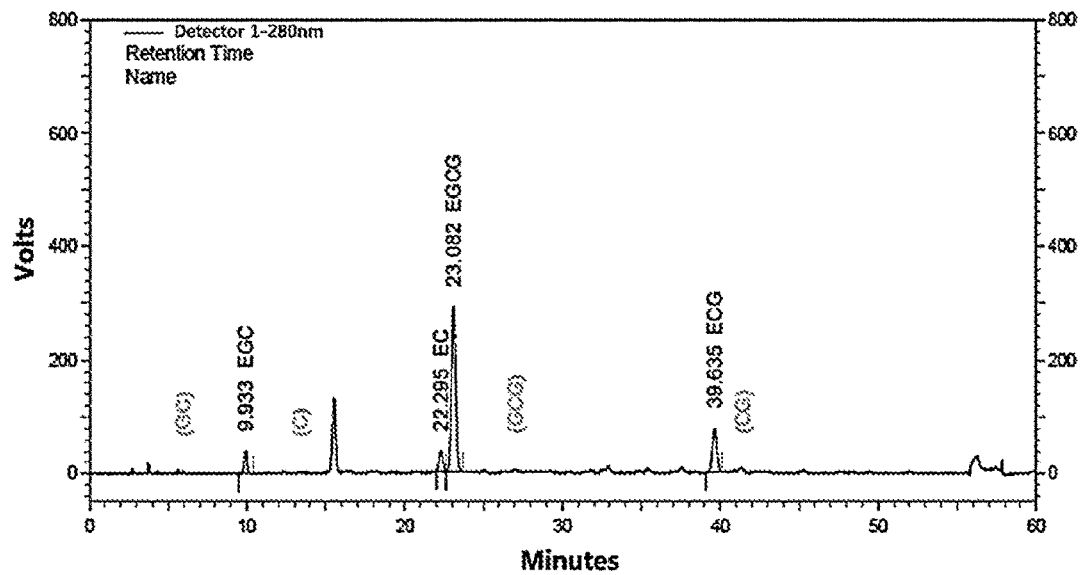
FIG. 1 shows a chromatogram for a notified green tea extract (Sample 1) of Example 1.

In the present specification, "green tea extract" includes an extract derived from a tea which is evergreen belonging to *Camellia sinensis* or an extract derived from tea leaf which was inoculated with *Bacillus subtilis* spp. and fermented, and includes a fraction obtained by fractionating the extract using a certain solvent, regardless of an extraction method, an extraction solvent, an extracted component or the form of the extract. The tea includes one or more selected from the group consisting of tea plant leaf, blossom, stem, fruit, root, branch, and heartwood of roots, and may preferably be leaf. In addition, the form of the extract may preferably be a powder form. The extraction or fraction can be performed using water, an organic solvent or a mixture solvent thereof. As the organic solvent, alcohol, isopropanol, acetone, hexane, ethyl acetate, carbon dioxide or a mixture solvent of two or more thereof can be used, but this is not limited thereto, and the extraction or fraction can be performed at a room temperature or by raising the temperature under a condition where the effective ingredient of the green tea is not destroyed or minimized. The alcohol may be a $C_1$ to $C_5$ lower alcohol. The frequency or method of the extraction or fraction is not particularly limited, and for example, methods such as cold extraction, ultrasonic extraction, reflux cooling extraction, hot water extraction, etc. can be used. Preferably, the green tea extract of the present disclosure can be obtained by extracting or fractionating and filtering the effective ingredient by cooling or heating, and then decompressing and concentrating the filtrate.

In the present specification, "epicatechin" includes epigallocatechin (EGC), (−)epicatechin (EC), (−)-epigallocatechin gallate (EGCG), and epicatechin 3-O-gallate (ECG).

In the present specification, "epicatechin epimer" includes gallocatechin (GC), catechin (C), (−)-gallocatechin gallate (GCG) and catechin gallate (CG).

In one aspect, the present disclosure may relate to a composition for preventing or improving skin wrinkles, comprising, as an effective ingredient, a green tea extract containing 4 to 15 wt. % of (−)-gallocatechin gallate (GCG) and 4 to 15 wt. % of (−)-epigallocatechin gallate (EGCG), on the basis of the total weight of the extract.

In another aspect, the present disclosure may relate to a composition for skin-whitening, comprising, as an effective ingredient, a green tea extract containing 4 to 15 wt. % of (−)-gallocatechin gallate (GCG) and 4 to 15 wt. % of (−)-epigallocatechin gallate (EGCG), on the basis of the total weight of the extract.

In one another aspect, the present disclosure may relate to a use of the green tea extract containing 4 to 15 wt. % of (−)-gallocatechin gallate (GCG) and 4 to 15 wt. % of (−)-epigallocatechin gallate (EGCG), on the basis of the total weight of the extract, for the preparation of the composition for preventing or improving skin wrinkles.

In one another aspect, the present disclosure may relate to a green tea extract containing 4 to 15 wt. % of (−)-gallocatechin gallate (GCG) and 4 to 15 wt. % of (−)-epigallocatechin gallate (EGCG), on the basis of the total weight of the extract, for the preparation of the composition for skin-whitening.

In one another aspect, the present disclosure may relate to a green tea extract containing 4 to 15 wt. % of (−)-gallocatechin gallate (GCG) and 4 to 15 wt. % of (−)- epigallocatechin gallate (EGCG), on the basis of the total weight of the extract, for use in preventing or improving skin wrinkles.

In one another aspect, the present disclosure may relate to a green tea extract containing 4 to 15 wt. % of (−)-gallocatechin gallate (GCG) and 4 to 15 wt. % of (−)-epigallocatechin gallate (EGCG), on the basis of the total weight of the extract, for use in skin-whitening.

In one another aspect, the present disclosure may relate to a method for preventing or improving skin wrinkles, comprising administering, to a subject in need thereof, a green tea extract containing 4 to 15 wt. % of (−)-gallocatechin gallate (GCG) and 4 to 15 wt. % of (−)-epigallocatechin gallate (EGCG), on the basis of the total weight of the extract.

In one another aspect, the present disclosure may relate to a method for skin-whitening, comprising administering, to a subject in need thereof, a green tea extract containing 4 to 15 wt. % of (−)-gallocatechin gallate (GCG) and 4 to 15 wt. % of (−)-epigallocatechin gallate (EGCG), on the basis of the total weight of the extract.

In one aspect, the GCG may be contained in the amount of 4 wt. % or more, 5 wt. % or more, 5.3 wt. % or more, 5.59 wt. % or more, 5.7 wt. % or more, 6 wt. % or more, 7 wt. % or more, 8 wt. % or more, 9 wt. % or more, 10 wt. % or more, 11 wt. % or more, 12 wt. % or more, 13 wt. % or more, or 14 wt. % or more, on the basis of the total weight of the extract. In another aspect, the GCG may be contained in the amount of 15 wt. % or less, 14 wt. % or less, 13 wt. % or less, 12 wt. % or less, 11 wt. % or less, 10 wt. % or less, 9 wt. % or less, 8 wt. % or less, 7 wt. % or less, 6 wt. % or less, 5.7 wt. % or less, 5.59 wt. % or less, 5.3 wt. % or less, or 5 wt. % or less, on the basis of the total weight of the extract. If the GCG is contained within said amount range, the composition may exhibit excellent MMP-1 inhibition activity, melanin production inhibition activity or tyrosinase activity inhibition effect.

In one aspect, the EGCG may be contained in the amount of 4 wt. % or more, 5 wt. % or more, 5.2 wt. % or more, 5.27 wt. % or more, 5.5 wt. % or more, 6 wt. % or more, 7 wt. % or more, 8 wt. % or more, 9 wt. % or more, 10 wt. % or more, 11 wt. % or more, 12 wt. % or more, 13 wt. % or more, or 14 wt. % or more, on the basis of the total weight of the extract. In another aspect, the EGCG may be contained in the amount of 15 wt. % or less, 14 wt. % or less, 13 wt. % or less, 12 wt. % or less, 11 wt. % or less, 10 wt. % or less, 9 wt. % or less, 8 wt. % or less, 7 wt. % or less, 6 wt. % or less, 5.5 wt. % or less, 5.27 wt. % or less, 5.2 wt. % or less or 5 wt. % or less, on the basis of the total weight of the extract.

As another embodiment, the total amount of GCG and EGCG in the extract may be 30 wt. % or less, on the basis of the total weight of the extract. In one aspect, the total amount of GCG and EGCG in the extract may be 30 wt. % or less, 25 wt. % or less, 20 wt. % or less, 18 wt. % or less, 16 wt. % or less, 15 wt. % or less, 14 wt. % or less, 12 wt. % or less, 10.5 wt. % or less, 10 wt. % or less, or 9 wt. % or less, on the basis of the total weight of the extract. In another aspect, the total amount of the GCG and the EGCG in the extract may be 8 wt. % or more, 9 wt. % or more, 10 wt. % or more, 10.5 wt. % or more, 12 wt. % or more, 13 wt. % or more, 14 wt. % or more, 16 wt. % or more, 18 wt. % or more, 20 wt. % or more, or 25 wt. % or more, on the basis of the total weight of the extract.

As another embodiment, the amount of epicatechin in the extract may be 20 wt. % or less, on the basis of the total weight of the extract. In one aspect, the amount of epicatechin in the extract may be 20 wt. % or less, 18 wt. % or less, 16 wt. % or less, 15 wt. % or less, 14 wt. % or less, 12 wt. % or less, 11 wt. % or less, or 10 wt. % or less, on the basis of the total weight of the extract. In another aspect, the amount of epicatechin in the extract may be 9 wt. % or more, 10 wt. % or more, 11 wt. % or more, 12 wt. % or more, 13 wt. % or more, 14 wt. % or more, 16 wt. % or more, or 18 wt. % or more, on the basis of the total weight of the extract.

As another embodiment, the total amount of 8 types of catechins in the extract, i.e. the total amount of EGCG, (−)-epigallocatechin (EGC), (−)epicatechin (EC), epicatechin 3-O-gallate (ECG), GCG, gallocatechin (GC), catechin (C) and catechin gallate (CG) in the extract may be from 19 to 30 wt. %, on the basis of the total weight of the extract. In one aspect, the total amount of the 8 types of catechins may be 19 wt. % or more, 21 wt. % or more, 23 wt. % or more, 24 wt. % or more, 24.5 wt. % or more, 25 wt. % or more, 26 wt. % or more, 27 wt. % or more, 28 wt. % or more, or 29 wt. % or more, on the basis of the total weight of the extract. In another aspect, the total amount of the 8 types of catechins may be 30 wt. % or less, 29 wt. % or less, 28 wt. % or less, 27 wt. % or less, 26 wt. % or less, 25 wt. % or less, 24.5 wt. % or less, 24 wt. % or less, 23 wt. % or less, or 21 wt. % or less, on the basis of the total weight of the extract.

As another embodiment, the weight ratio of GCG:EGCG in the extract may be 1:0.5 to 2. In one aspect, the weight ratio of GCG:EGCG in the extract may be 1:0.5, 1:0.8, 1:1, 1:1.2, 1:1.5, 1:1.8 or 1:2.

As one another embodiment, the extract may be an extract obtained by extracting using one or more of water and C1 to C4 alcohol one or more times. In one aspect, the alcohol may be ethanol. In another aspect, the alcohol may be ethanol of 20% or more, 30% or more, 40% or more, 50% or more, 60% or more or 70% or more. In another aspect, the alcohol may be ethanol of 70% or less, 60% or less, 50% or less, 40% or less or 30% or less.

As another embodiment, the amount of the green tea extract in the composition for preventing or improving skin wrinkles may be from 1 wt. % to 100 wt. % relative to the total weight of the composition. In one aspect, the amount of the extract in the composition may be 1 wt. % or more, 10 wt. % or more, 20 wt. % or more, 30 wt. % or more, 40 wt. % or more, 50 wt. % or more, 60 wt. % or more, 70 wt. % or more, 80 wt. % or more or 90 wt. % or more. In another aspect, the amount of the extract in the composition may be 100 wt. % or less, 90 wt. % or less, 80 wt. % or less, 70 wt. % or less, 60 wt. % or less, 50 wt. % or less, 40 wt. % or less, 30 wt. % or less or 20 wt. % or less.

As another embodiment, the dosage of the effective ingredient may be from 5 mg/kg/day to 1000 mg/kg/day. In one aspect, the dosage may be 5 mg/kg/day or more, 100 mg/kg/day or more, 200 mg/kg/day or more, 300 mg/kg/day or more, 400 mg/kg/day or more, 500 mg/kg/day or more, 600 mg/kg/day or more, 700 mg/kg/day or more, 800 mg/kg/day or more, or 900 mg/kg/day or more. In another aspect, the dosage may be 1000 mg/kg/day or less, 900 mg/kg/day or less, 800 mg/kg/day or less, 700 mg/kg/day or less, 600 mg/kg/day or less, 500 mg/kg/day or less, 400 mg/kg/day or less, 300 mg/kg/day or less, 200 mg/kg/day or less, 100 mg/kg/day or less, 50 mg/kg/day or less, or 10 mg/kg/day or less.

As one embodiment, the extract can inhibit the expression of MMP-1 (matrix metalloproteinase-1). In other words, the extract or composition can exhibit the effect of preventing or improving skin wrinkles by inhibiting the expression of MMP-1.

As another embodiment, the extract can inhibit melanin production, and as one another embodiment, the extract can inhibit the activity of tyrosinase. In other words, the extract or composition can exhibit the effect of skin-whitening by inhibiting melanin production or inhibiting the activity of tyrosinase.

As one embodiment, the composition may be a food, pharmaceutical or cosmetic composition.

The formulation of the food composition is not particularly limited, but the food composition may be formulated into, for example, tablets, granules, pills, powders, solutions such as drinks, caramels, gels, bars, tea bags, etc. In the food composition of the respective formulations, in addition to the effective ingredient, ingredients typically used in the pertinent field can be suitably selected and mixed by a person skilled in the art without any difficulty depending on the formulation or purpose of use, and when this composition is applied together with other raw material, a synergistic effect would be generated. In addition, the food may be health functional food.

The composition may be administered by various methods, such as simple intake, drinking, injection administration, spray administration, or squeeze administration.

In the food composition according to one aspect of the present disclosure, the determination of the dosage of the effective ingredient is made at the level of a person skilled in the art, and may vary depending on various factors such as age, health conditions, complications, etc. of the subject to which the composition is administered.

The food composition according to one aspect of the present disclosure may be health functional food such as chewing gums, caramels, candies, ice creams, snacks, breads, etc., and beverage products such as soft drink, mineral water, alcoholic drinks, etc., and functional foods including vitamin or mineral, etc.

Other than the above, the food composition according to one aspect of the present disclosure may include several nutritional supplements, vitamins, minerals (electrolyte), flavoring agents such as synthetic flavoring agents and natural flavoring agents, colorants and enhancers (cheese, chocolate, etc.), pectic acids and salts thereof, alginic acids and salts thereof, organic acids, protective colloid thickeners, pH regulators, stabilizers, preservatives, glycerin, alcohol, carbonation used for carbonated beverages, and the like. In addition, the food compositions according to one aspect of the present disclosure may include natural fruit juices and fruit pulps for the preparation of fruit juice drink and vegetable drink. Such ingredients may be used independently or in combination. The ratio of such additives is not important, but the additives are generally comprised in the amount ranging from 0 to about 60 parts by weight per 100 parts by weight of the composition according to one aspect of the present disclosure.

The pharmaceutical composition according to one aspect of the present disclosure can be administered orally, parenterally, rectally, topically, transdermally, intravenously, intramuscularly, intraperitoneally, subcutaneously, etc. The formulation for the oral administration may be tablets, pills, soft and hard capsules, granules, powders, fine granules, solutions, emulsifying agents or pellets, but not limited thereto. The formulation for the parenteral administration may be solutions, suspensions, liquids, gels, injections, drops, suppository, patches or sprays, but not limited thereto. The formulations can be easily prepared according to the typical method in the pertinent field, and may further comprise surfactants, excipients, wettable powders, emulsifiers, suspensions, salts or buffers for osmotic pressure control, colorants, spices, stabilizers, antimicrobial agents, preservatives, or other commercial auxiliaries.

The composition according to one aspect of the present disclosure may comprise pharmaceutically acceptable salts, wherein the salts may include (1) acid addition salts that are formed from inorganic acids such as hydrochloric acids, hydrobromic acids, sulfuric acids, nitric acids, phosphoric acids, or the like; or formed from organic acids such as acetic acids, propionic acids, hexanoic acids, cyclopentanepropionic acids, glycolic acids, pyruvic acids, lactic acids, malonic acids, succinic acids, malic acids, maleic acids, fumaric acids, tartaric acids, citric acids, benzoic acids, 3-(4-hydroxybenzoyl) benzoic acids, cinnamic acids, mandelic acids, methanesulfonic acids, ethanesulfonic acids, 1,2-ethane-disulfonic acids, 2-hydroxyethanesulfonic acids, benzenesulfonic acids, 4-chlorobenzenesulfonic acids, 2-naphthalenesulfonic acids, 4-toluenesulfonic acids, camphorsulfonic acids, 4-methylbicyclo [2,2,2]-oct-2-ene-1-carboxylic acids, glucoheptonic acids, 3-phenylpropionic acids, trimethylacetic acids, tert-butylacetic acids, lauryl sulfuric acids, gluconic acids, glutamic acids, hydroxynaphthoic acids, salicylic acids, stearic acids, and muconic acids; or (2) salts formed when acidic protons present in the parent compound are substituted.

The amount or dosage of the pharmaceutical composition used according to one aspect of the present disclosure may vary depending on age, gender and weight, pathology and its severity of the subject to which the composition is administered, dosing route and prescriber's decision. The determination of the dosage based on such factors is made at the level of a person skilled in the art.

The cosmetic composition according to one aspect of the present disclosure may contain cosmetically or dermatologically acceptable medium or base. This may be provided in all of formulations suitable for topical application, for example, solutions, gels, solid, pasty anhydride products, emulsions obtained by dispersing an oily phase into an aqueous phase, suspensions, microemulsions, microcapsules, fine granules or ionic (liposome) and non-ionic sacculated dispersions, or creams, skins, lotions, powders, ointments, sprays or conceal sticks. These compositions may be prepared according to the typical method in the pertinent field. The cosmetic composition may also be used in the form of an aerosol composition further containing a propellant compressed in the form of foam.

The formulation of the cosmetic composition is not particularly limited, and can be suitably selected depending on the purpose. For example, the cosmetic composition can be prepared in the formulation of, for example, skin lotion, skin softener, skin toner, lotion, milk lotion, moisture lotion, nourishing lotion, massage cream, nourishing cream, moisture cream, hand bream, foundation, essence, nourishing essence, pack, soap, cleansing foam, cleansing lotion, cleansing cream, cleansing water, powder, body lotion, body cream, body oil, body cleanser and body essence, etc.

In case where the formulation of the present disclosure is paste, cream or gel, animal fiber, vegetable fiber, wax, paraffin, starch, tragacanth, cellulose derivative, polyethylene glycol, silicon, bentonite, silica, talc or zinc oxide, etc. may be used as a carrier ingredient.

In case where the formulation of the present disclosure is power or spray, lactose, talc, silica, aluminum hydroxide, calcium silicate or polyamide powder may be used as a carrier ingredient, and particularly, in the case of spray, the composition may further comprise propellants such as chlorofluorohydrocarbon, propane/butane or dimethyl ether.

In case where the formulation of the present disclosure is a solution or an emulsion, a solvent, a solvating agent or a emulsifier is used as a carrier ingredient, and the examples thereof include water, ethanol, isopropanol, ethyl carbonate, ethyl acetate, benzyl alcohol, benzyl benzoate, propylene glycol, 1,3-butylglycol oil, glycerol fatty acid, polyethylene glycol or fatty acid ester of sorbitan.

In case where the formulation of the present disclosure is a suspension, a liquid diluent such as water, ethanol or propylene glycol, suspensions such as ethoxylated isostearyl alcohol, polyoxyethylene sorbitol ester and polyoxyethylene sorbitan ester, microcrystalline cellulose, aluminum metahydroxide, bentonite, agar-agar or tragacanth, etc. may be used as a carrier ingredient.

In case where the formulation of the present disclosure is a surfactant-containing cleansing, aliphatic alcohol sulfate, aliphatic alcohol ether sulfate, sulfosuccinic monoester, isethionate, imidazolinium derivatives, methyltauride, sarcosinate, fatty acid amide ether sulphate, alkylamidobetaine, fatty alcohols, fatty acid glycerides, fatty acid diethanolamide, vegetable oil, lanolin derivatives, or ethoxylated glycerol fatty acid ester, etc. may be used as a carrier ingredient.

The cosmetic composition may further include, in addition to the green tea extract, functional additives and ingredients that are comprised in general cosmetic compositions. The examples of the functional additives may include ingredient selected from the group consisting of water-soluble vitamins, oil-soluble vitamins, polypeptide, polysaccharide, sphingolipid and plant extracts.

In addition, in the composition, ingredients that are comprised in general cosmetic composition, other than the aforementioned functional additives, can be suitably mixed as needed. The examples of the additionally comprised ingredients to be mixed include fat, a moisturizing agent, an emollient, a surfactant, organic and inorganic pigments, organic powders, an ultraviolet absorbent, an antimicrobial agent, a sterilizer, an antioxidant, a plant extract, a pH regulator, alcohol, a colorant, a flavoring agent, a blood circulation promoter, a cooling agent, an antiperspirant, a purified water, etc.

EXAMPLES

Hereinafter, the constitution and effect of the present specification will be explained in more detail with reference to the examples, test examples and formulation examples. However, these examples are provided only for the purpose of illustration in order to help the understanding of the present specification, and the scope and range of the present specification are not limited thereto.

Example 1

Preparation of General Notified Green Tea Extract and the High Temperature-Processed Green Tea Extract 1000 ml of 50% ethanol was added to 100 g of green tea (*Camellia sinensis*; O'sulloc in Jeju), and then refluxed and stirred at 60° C. for 1 hour. A solution, which was obtained by lowering the temperature of the sample to a room temperature and filtering, was decompressed and distilled to obtain 20 g of dark brown powder of general notified green tea extract (GT-LE-35CAT, Sample 1) (yield 23%).

On the other hand, in order to prepare a high temperature-processed green tea extract, 1000 ml of 50% ethanol was added to 100 g of green tea (*Camellia sinensis*; O'sulloc in Jeju), and then refluxed and stirred at 60° C. for 1 hour. This was concentrated and then stirred at 1.5 kgf/cm$^2$ of steam for 1-7 hours. Thereafter, 10 g of a high temperature-processed green tea extract was obtained by lowering the temperature to a room temperature, filtering insoluble substances, and decompressing and concentrating it. Herein, the change of the amounts of the 8 types of catechins in the high temperature-processed green tea extract obtained at each stirring time (1-7 hours) was measured using the device shown in the following Table 1, and it was verified that at 5 hours, the conversion from EGCG into GCG by heat was the most, and the amounts of the 8 types of catechins were not reduced anymore. The resultant 10 g of high temperature-processed green tea extract (HTP-GTE) was used as Sample 2.

Figure 2:
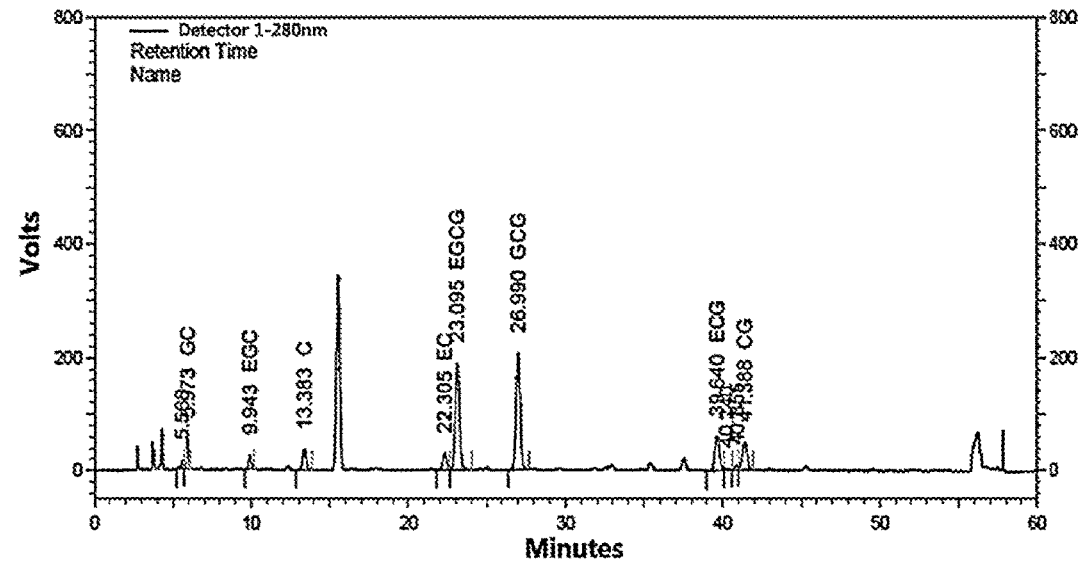
FIG. 2 shows a chromatogram for a high temperature-processed green tea extract (Sample 2) according to one aspect of the present disclosure.

The conditions and results of the analysis of the two types of extracts obtained therefrom are shown in the following Table 1 (composition analysis conditions of Samples 1 and 2), Table 2 (composition analysis results of Sample 1) and Table 3 (composition analysis results of Sample 1), respectively. In addition, the chromatograms of the two types of extracts are shown in FIG. 1 (Sample 1) and FIG. 2 (Sample 2). From the above, it was verified that the composition of Sample 2 is different from that of the typical green tea extract. Specifically, it was verified that while Sample 2 contained EGCG (5.27 wt. %), EGC (3.53 wt. %) and total catechins (24.41 wt. %) in significantly lower amounts as compared to Sample 1, Sample 2 additionally produced 4 types of epicatechin epimers that were not found in Sample 1.

TABLE 1

| Column | Thermofisher C18 5 um, 4.6 × 250 mm |
|---|---|
| Detector | UV 280 nm |
| Dilution | Water in Gradient A-0.1% TFA (Trifluoro acetic acid) |
| | B-Acetonitrile |
| Gradient profile | 0 min A(90):B(10) |
| | 30 min A(85):B(15) |
| | 42 min A(80):B(20) |
| | 44 min A(5):B(95) |
| | 49 min A(90):B(10) |
| Flow rate | 1 ml/min |
| Injection volume | 20 μl |

TABLE 2

| | GC | EGC | Caffeine | C | EC | GCG | EGCG | CG | ECG | Total amounts of epicatechins | Total amounts of epicatechin epimers | Total amounts of 8 types |
|---|---|---|---|---|---|---|---|---|---|---|---|---|
| Sample 1 | 0 | 9.16 | 3.21 | 0 | 3.63 | 0 | 20.93 | 0 | 2.62 | 36.34 | 0 | 36.34 |

TABLE 3

| | GC | EGC | Caffeine | C | EC | GCG | EGCG | CG | ECG | Total amounts of epicatechins | Total amounts of epicatechin epimers | Total amounts of 8 types |
|---|---|---|---|---|---|---|---|---|---|---|---|---|
| Sample 2 | 4.9 | 3.53 | 3.9 | 1.57 | 0.95 | 5.59 | 5.27 | 1.3 | 1.3 | 11.05 | 13.36 | 24.41 |

(In Tables 2 and 3, GC is gallocatechin, EGC is epigallocatechin, C is catechin, EC is (−)epicatechin, GCG is gallocatechin gallate, EGCG is epigallocatechin gallate, CG is catechin gallate, and ECG is epicatechin 3-O-gallate.)

(The units of Tables 2 and 3 are all wt. % of the corresponding ingredient relative to the total weight of the green tea extracts (Samples 1 and 2).)

Test Example 1

Evaluation Test of MMP-1 (Matrix Metalloproteinase-1) Inhibition Activity

The evaluation on MMP-1 inhibition activity was conducted in order to verify the effects of the green tea extracts of Samples 1 and 2 of Example 1 in inhibiting the production of MMP-1, which is skin tissue breakdown enzyme, in human skin fibroblast of aged human skin and in inhibiting the production of MMP-1 according to the weight ratio of EGCG and GCG, and the amount of GCG. To be specific, the evaluation was conducted through the following steps.

1-1. Culturing Cell Lines and Cells

Normal human dermal fibroblast (NHDF; Lonza, Switzerland) was cultured in a DMEM medium (Dulbecco's modified Eagle's Medium, Gibco 1210-0038) comprising 10% of fetal bovine serum, and the culturing was all performed in a 37° C., 5% $CO_2$ culture medium. Cells that had 6-9 sub-culture frequencies were used as young cells, and aged dermal fibroblasts were obtained by sub-culturing 37 times in such a manner that the number of cells was calculated for every sub-culture and then ⅕ of the total number of cells were newly cultured. The aged dermal fibroblasts were treated with EGCG and GCG depending on the ratio of EGCG:GCG and the concentration of GCG, or treated with Sample 1 or Sample 2.

1-2. Measuring the Amount of MMP-1 Produced

In order to verify the amount of MMP-1 produced, the enzyme-linked immunosorbent assay (ELISA) method was used (Amersham, USA). The culture medium of the cells treated with the samples at the step 1-1 was collected and the supernatant was isolated by centrifuging at 1000×g, and then the culture medium was put into a 96-well plate coated with an MMP-1 antibody, and then a secondary antibody (horse reddish peroxidase, HRP) was reacted at room temperature for 1 hour, and washed with 100 μL PBS. The amount of MMP-1 produced was confirmed by measuring absorbance at a 490 nm wavelength after reaction and confirming its degree of color formation using a TMB substrate solution (Pierce, USA), and the MMP-1 inhibition activity (%) was calculated using the following equation.

MMP-1 inhibition activity (%)=(O.D. of the group treated with the sample at 490 nm/O.D. of the group not treated with sample at 490 nm)×100

The results are shown in the following tables 4 and 5.

TABLE 4

| | | MMP-1 inhibition activity (%) | |
|---|---|---|---|
| | Treated amount (μg/ml) | Processed immediately | Processed after 24 hours |
| Sample 1 | 200 | 66 ± 10.2 | 10 ± 1.0 |
| Sample 2 | 200 | 83 ± 12.1 | 78 ± 6.9 |

TABLE 5

| Amount (μg/ml) | | | MMP-1 inhibition activity (%) | |
|---|---|---|---|---|
| EGCG | GCG | EGCG:GCG | Processed immediately | Processed after 24 hours |
| 3 | 0 | — | 56 ± 9.7 | 6 ± 1.0 |
| 2.4 | 0.6 | 4:1 | 53 ± 5.4 | 9.4 ± 0.9 |
| 2 | 1 | 2:1 | 67 ± 6.1 | 22 ± 1.1 |
| 1.8 | 1.2 | 1.5:1 | 76 ± 5.2 | 54 ± 3.1 |
| 1.5 | 1.5 | 1:1 | 74 ± 4.2 | 57 ± 0.8 |
| 1.2 | 1.8 | 1:1.5 | 73 ± 3.7 | 60 ± 6.3 |
| 0 | 3 | — | 55 ± 9.2 | 10 ± 1.0 |

From the result of Table 4, it was verified that the high temperature-processed green tea extract (Sample 2), comprising GCG in the amount of 5.59 wt. %, EGCG in the amount of 5.27 wt. %, epicatechin in the amount of 11.05 wt. %, epicatechin epimers in the amount of 13.36 wt. %, and 8 types of catechin in the total amount of 24.41 wt. %, had the excellent inhibition activity of MMP-1 as compared to the typical green team extract (Sample 1). In particular, it was verified that in case where the aged fibroblast was left at a room temperature for 24 hours and then processed, the MMP-1 inhibition activity of the high temperature-processed green tea extract according to the present disclosure was significantly superior, despite that the total amount of the 8 types of catechin was lower than the typical green tea extract.

In addition, from the result of Table 5, it was verified that in case where the weight ratio of EGCG:GCG is 2:1, 1.5:1, 1:1 or 1:1.5, it exhibited excellent MMP-1 inhibition activity as compared to the case where only EGCG was treated, only GCG was treated, or where the weight ratio of EGCG:GCG is 4:1. Particularly, in case where the weight ratio of EGCG:GCG is 1.5:1, 1:1 or 1:1.5, it exhibited more excellent MMP-1 inhibition activity.

As the result, it was confirmed that the high temperature-processed green tea extract comprising 4 to 15 wt. % of GCG and 4 to 15 wt. % of EGCG according to the present disclosure can effectively prevent or improve skin wrinkles through excellent MMP-1 inhibition activity, and in addition, it was confirmed that when the composition comprises GCG and EGCG in certain weight ratio according to the present disclosure, the effect of preventing or improving skin wrinkles through MMP-1 inhibition activity would be more improved.

Test Example 2

Test for Cell Cytotoxicity of the High Temperature-Processed Green Tea Extract Melanocyte cell lines (skin cytoma) obtained from Lonza were seeded in a 96-well plate (FALCON) at $1\times10^5$ per well, and cultured in a 37° C., 5% $CO_2$ incubator for 24 hours, and then it was treated with the high temperature-processed green tea extract of Example 1 (Sample 2) in the amounts of 10 ppm and 100 ppm and then further cultured for 48 hours.

Thereafter, the medium was removed, and the survival rate of the cells was verified using cell counting kit-8 (Dojindo). 10 μl of cell counting kit-8 (Dojindo) solution was added to 100 μl of RPMI1640 (Lonza) to process the cells, then absorbance was confirmed at 450 nm, and then the number of living cells was quantified. The number of cells or the cell viability (%) was calculated by the following equation.

Cell viability (%)=(absorbance of the group treated with the sample−absorbance of reaction reagent only)/(absorbance of the group not treated with sample−absorbance of reaction reagent only)×100

Figure 3:
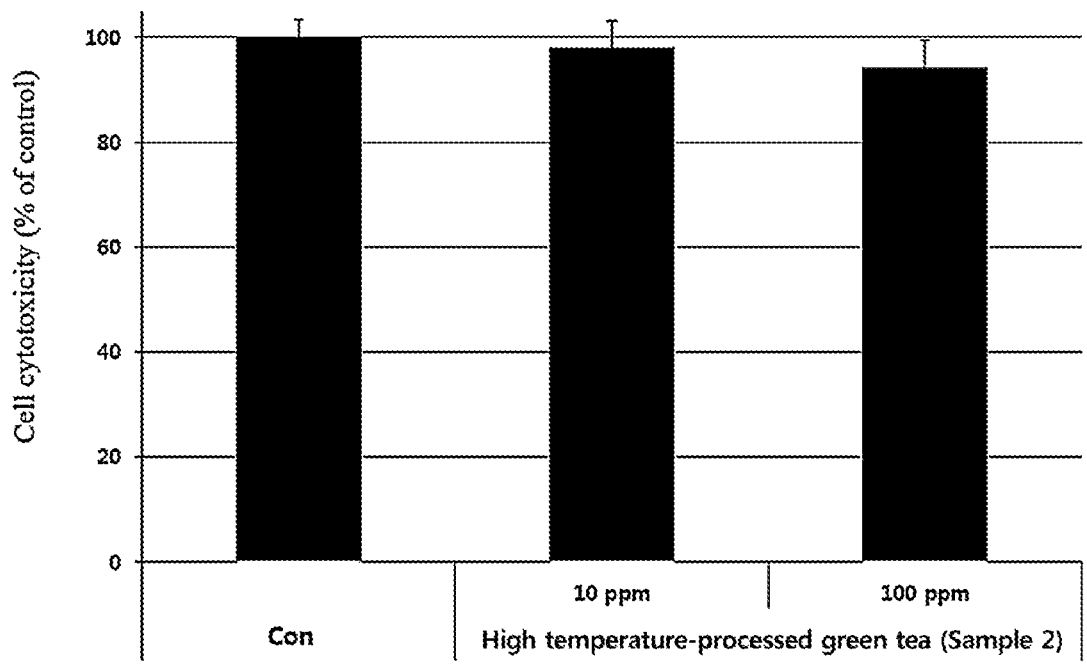
FIG. 3 shows the test results of cell cytotoxicity of the high temperature-processed green tea extract according to Test Example 2.

The result is shown in FIG. 3, and it was verified that both 10 ppm and 100 ppm of the high temperature-green tea extracts (Sample 2) exhibited no cell cytotoxicity.

Test Example 3

Evaluation of the High Temperature-Processed Green Tea Extract in Inhibiting the Production of Melanin The MNT-1 cells, which are human melanoma cell lines (Lonza, SWISS) with overproduction of melamine, were seeded in a 6-well plate at $1\times10^6$ cell/well, cultured for 24 hours under the 37° C., 5% $CO_2$ conditions, then treated with Sample 1 and Sample 2 of Example 1 in the amounts of 10 ppm and 100 ppm, and cultured a 37° C., 5% $CO_2$ incubator for 48 hours. The cell cultured for 48 hours was processed with 500 μl of Lysis Buffer (1% NP-40, 50 mM Tris-HCL; pH 7.5, 150 mM NaCl), collected in a microtube using a cell scraper, and then centrifuged at 13,000 rpm for 15 minutes (Eppendorf, centrifuge 5415R, Germany). Thereafter, the precipitates were isolated and dissolved using 50 μl of 1N sodium hydroxide, and then absorbance was measured at a 450 nm wavelength specific to melanin was measured and the amount of melanin was corrected to the total amount of proteins according to the following equation. Herein, as a control, MNT-1 cell, which was not treated with the sample, was used, and the result is shown in FIG. 4.

Amount of melanin (%)=absorbance/the total amount of proteins

Figure 4:
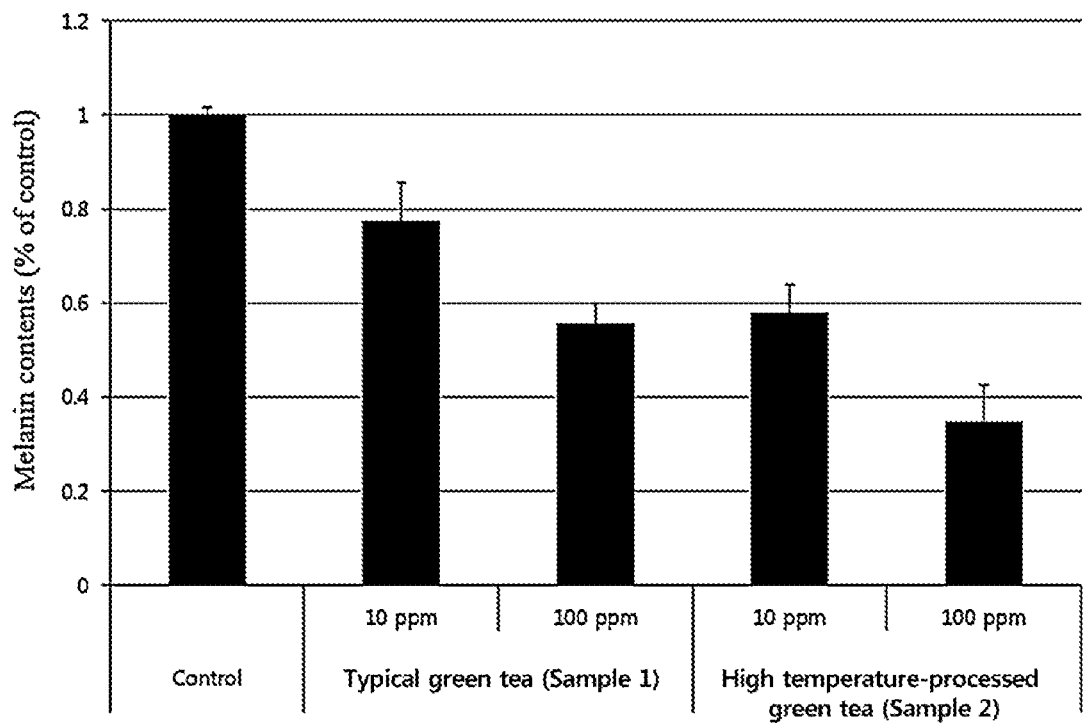
FIG. 4 shows the evaluation results of the effect of the high temperature-processed green tea extract in inhibiting the production of melanin cells according to Test Example 3.

From the result of FIG. 4, it was verified that as compared to the typical green tea extract (Sample 1), the high temperature-processed green tea extract (Sample 2) was much excellent in inhibiting melanin production.

In particular, in case where 100 ppm of the high temperature-processed green tea extract was treated, the effect of inhibiting melanin production was significantly high. In addition, in case where 10 ppm of the high temperature-processed green tea extract was treated, the effect of inhibiting melanin production was similar to the case of being treated with 100 ppm of the typical green tea extract. From this result, it was confirmed that the effect of the high temperature-processed green tea extract according to the present disclosure in inhibiting melanin production is 10 times more excellent than the typical green tea extract.

Test Example 4

Evaluation of the High Temperature-Processed Green Tea Extract in Inhibiting Tyrosinase Activity 10 mM of DOPA (dihydroxyphenylalanine) (equivalent amount 10 μg) was added to 10 μg of cell dissolution according to Test Example 2, and the amount of dopachrome produced by the action of tyrosinase was measured by comparing absorbance at 490 nm. The tyrosinase activity was calculated as the ratio to the absorbance of the group not treated with sample, and then shown in FIG. 5.

Figure 5:
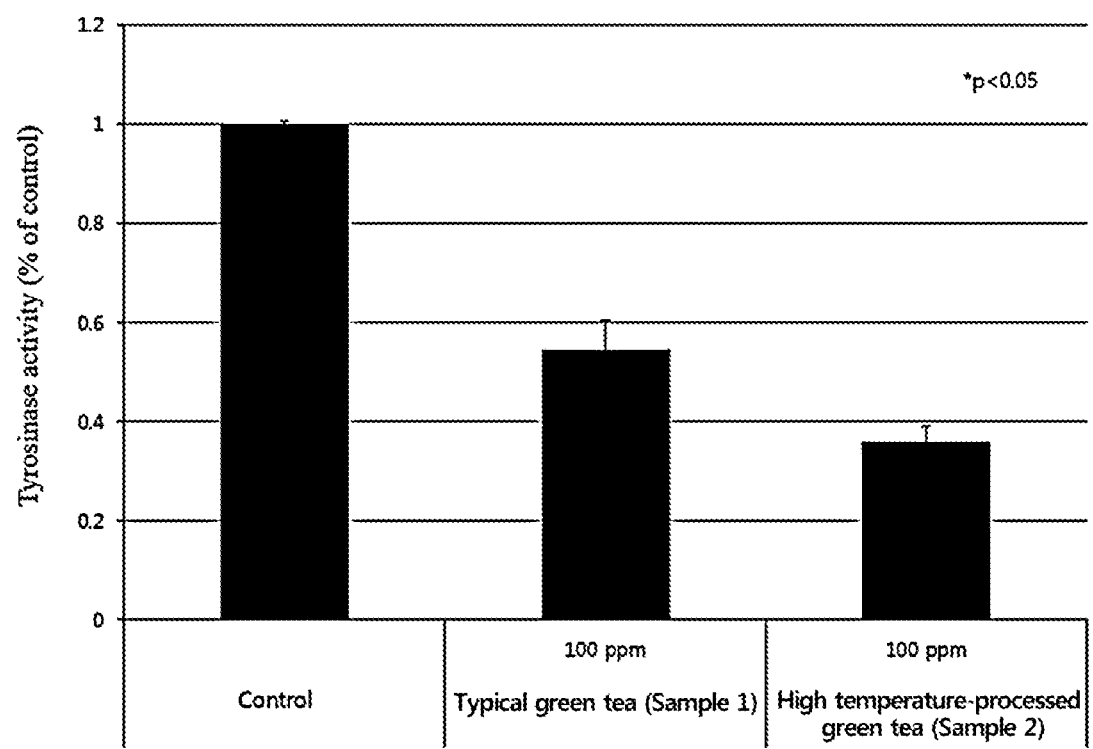
FIG. 5 shows the evaluation results of the effect of the high temperature-processed green tea extract in inhibiting tyrosinase activity according to Test Example 4.

From the result of FIG. 5, it was verified that the high temperature-processed green tea extract according to the present disclosure has much excellent effect of inhibiting tyrosinase activity as compared to the typical green tea extract.

Formulation Example 1

Soft Capsule 150 mg of Sample 2 according to Example 1 was prepared, and mixed with 440 mg of lactose, 430 mg of cornstarch, and 2 mg of magnesium stearate to prepare a soft capsule filling solution. Thereafter, separately from the above, a soft capsule sheet was prepared at the ratio of 66 parts by weight of gelatin, 24 parts by weight of glycerin, and 10 parts by weight of sorbitol solution and filled with the filling solution to prepare a soft capsule.

Formulation Example 2

Tablet 150 mg of Sample 2 according to Example 1 was prepared, mixed with 15 mg of vitamin E, 15 mg of vitamin C, 250 mg of galactooligosaccharide, 60 mg of milk sugar. and 140 mg of malt sugar, then granulated using a fluidized bed drier, and then 8 mg of sugar ester was added. The tablet was prepared by tableting this composition by a typical method.

Formulation Example 3

Drink 80 mg of Sample 2 according to Example 1 was prepared, mixed with 9 mg of vitamin E, 9 mg of vitamin C, 10 g of glucose, 0.6 g of citric acid, and 25 g of liquid oligosaccharide, and then filled by adding 400 ml of purified water. After filling it in the bottle, the bottle was sterilized for 4-5 seconds at 30° C. to prepare the drink.

Formulation Example 4

Granule

A granule was prepared by preparing 150 mg of Sample 2 according to Example 1, mixing it with 9 mg of vitamin E, 9 mg of vitamin C, 250 mg of anhydrous crystalline glucose, and 550 mg of starch, then molding it in granules using a fluidized bed granulator, and then filling it in a pouch.

Formulation Example 5

Health Food 150 mg of Sample 2 according to Example 1 was prepared, mixed with vitamin mixtures (70 μg of vitamin A acetate, 1.0 mg of vitamin E, 0.13 mg of vitamin B1, 0.15 mg of vitamin B2, 0.5 mg of vitamin B6, 0.2 μg of vitamin B12, 10 mg of vitamin C, 10 μg of biotin, 1.7 mg of nicotine acid amide, 50 μg of folic acid) and mineral mixture (1.75 mg of ferrous sulfate, 0.82 mg of zinc oxide, 25.3 mg of magnesium carbonate, 15 mg of potassium phosphate monobasic, 55 mg of potassium phosphate polybasic, 90 mg of potassium citrate, 100 mg of calcium carbonate, 24.8 mg of magnesium chloride) to prepare health food.

Formulation Example 6

Health Beverage 50 mg of Sample 2 according to Example 1 was prepared, and mixed with 1000 mg of citric acid, 100 g of oligosaccharide, 2 g of plum concentrate, 1 g of taurine, and the balance of purified water to prepare 900 mL of health beverage.

Formulation Example 7

Ample 10 mg of Sample 2 according to Example 1 was prepared, mixed with maltodextrin, then 15 ml of purified water was added, and filled in an ample bottle. The bottle was sterilized to prepare a liquid ample.

The extract and composition according to one aspect of the present disclosure are derived from natural plants that cause less irritation to the skin and are eco-friendly, thus they are safe, and thereby the extract and composition can exhibit excellent effects of effectively inhibiting the expression of MMP-1 and preventing or improving skin wrinkles.

In addition, the extract and composition according to one aspect of the present disclosure are derived from natural plants that cause less irritation to the skin and are eco-friendly, thus they are safe, and thereby the extract and composition can exhibit excellent effects of effectively inhibiting melanin production and tyrosinase activity and preventing or improving skin whitening.

While the present disclosure has been described with respect to the specific embodiments, it will be apparent to those skilled in the art that various changes and modifications may be made without departing from the spirit and scope of the invention as defined in the following claims.

What is claimed is:

1. A method for whitening human skin in need thereof comprising: administering, to a human in need thereof, a steam-processed green tea extract containing 4 to 15 wt. % of (−)-gallocatechin gallate (GCG) and 5.27 to 15 wt. % of (−)-epigallocatechin gallate (EGCG), on the basis of the total weight of the extract, wherein the weight ratio of GCG: EGCG in the extract is 1:0.5 to 1:2, and wherein administering the green tea extract exhibits inhibition activity of tyrosinase in the human and wherein the total amount of EGCG, epigallocatechin (EGC), (−)epicatechin (EC), epicatechin 3-O-gallate (ECG), GCG, gallocatechin (GC), catechin (C) and catechin gallate (CG) in the extract are from 21 to 30 wt. %, on the basis of the total weight of the extract.

2. The method according to claim 1, wherein the total amount of EGCG, epigallocatechin (EGC), (−) epicatechin (EC), epicatechin 3-O-gallate (ECG), GCG, gallocatechin (GC), catechin (C) and catechin gallate (CG) in the extract are from 19 to 30 wt. %, on the basis of the total weight of the extract.

3. The method according to claim 1, wherein the weight ratio of GCG: EGCG in the extract is 1:0.5 to 2.

4. The method according to claim 1, wherein the extract is an extract obtained by extracting with one or more of water and C1 to C4 alcohol one or more times.

5. The method according to claim 1, wherein the green tea extract is formulated in a form of a composition, wherein the amount of the extract in the composition is from 1 wt. % to 100 wt. % relative to the total weight of the composition.

6. The method according to claim 1, wherein the dosage of the green tea extract is from 5 mg/kg/day to 1000 mg/kg/day.

7. The method according to claim 1, wherein the extract inhibits melanin production.

8. The method according to claim 1, wherein the extract inhibits the activity of tyrosinase.

9. The method according to claim 1, wherein the green tea extract is formulated in a form of a composition, wherein the composition is a food, pharmaceutical or cosmetic composition.

* * * * *